United States Patent [19]
Garza

[11] Patent Number: 5,806,089
[45] Date of Patent: Sep. 15, 1998

[54] REVERSIBLE VISOR AND ASSEMBLY METHOD THEREFOR

[75] Inventor: Irene E. Garza, San Antonio, Tex.

[73] Assignee: Texace

[21] Appl. No.: 708,850

[22] Filed: Sep. 9, 1996

Related U.S. Application Data

[62] Division of Ser. No. 410,880, Mar. 27, 1995, Pat. No. 5,581,808.
[51] Int. Cl.⁶ .......................................................... A61F 9/00
[52] U.S. Cl. .................................... 2/12; 2/171; 2/209.11; 2/209.3; 2/DIG. 2
[58] Field of Search ................................. 2/12, 171, 181, 2/183, 184, 209.11, 209.3, 209.4, DIG. 2, DIG. 11

[56] References Cited

U.S. PATENT DOCUMENTS 4,686,713  8/1987  Coleman et al. .............................. 2/12

*Primary Examiner*—Diana Biefeld
*Attorney, Agent, or Firm*—Donald R. Comuzzi; Christopher L. Makay

[57] ABSTRACT

A convertible visor has a bill including a first bill covering attached to a second bill covering with a bill stiffener therebetween. The bill stiffener permits the reversing of the bill to display either the first bill covering or the second bill covering as the exterior of the visor. A headband attaches to the bill and includes a first headband covering attached to a second headband covering. The first and second headband coverings define an enclosure therebetween that contains a headband stiffener. Furthermore, the first and second headband coverings are rotatable about the headband stiffener to permit the display of either the first headband covering or the second headband covering as the exterior of the visor.

4 Claims, 5 Drawing Sheets

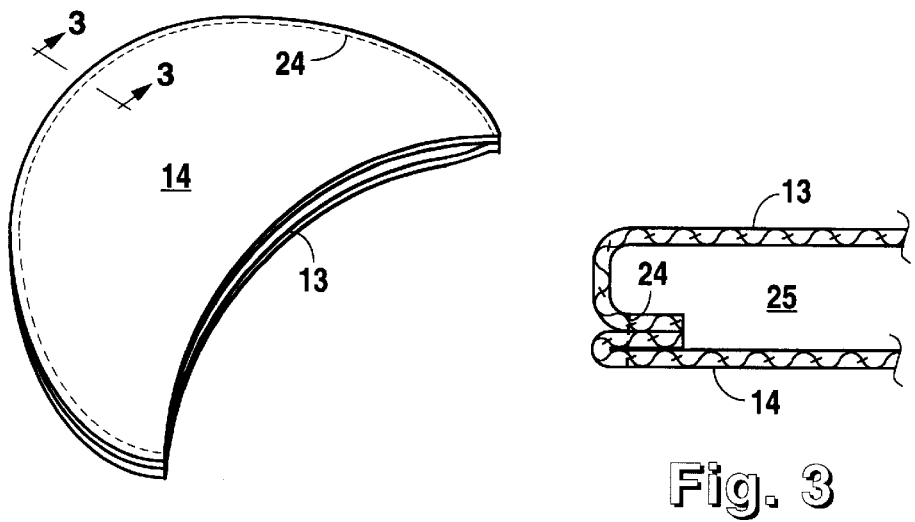
Fig. 2
Fig. 3
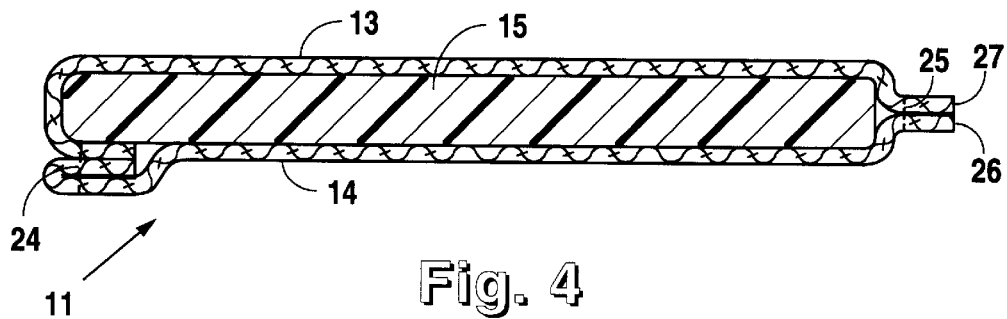
Fig. 4
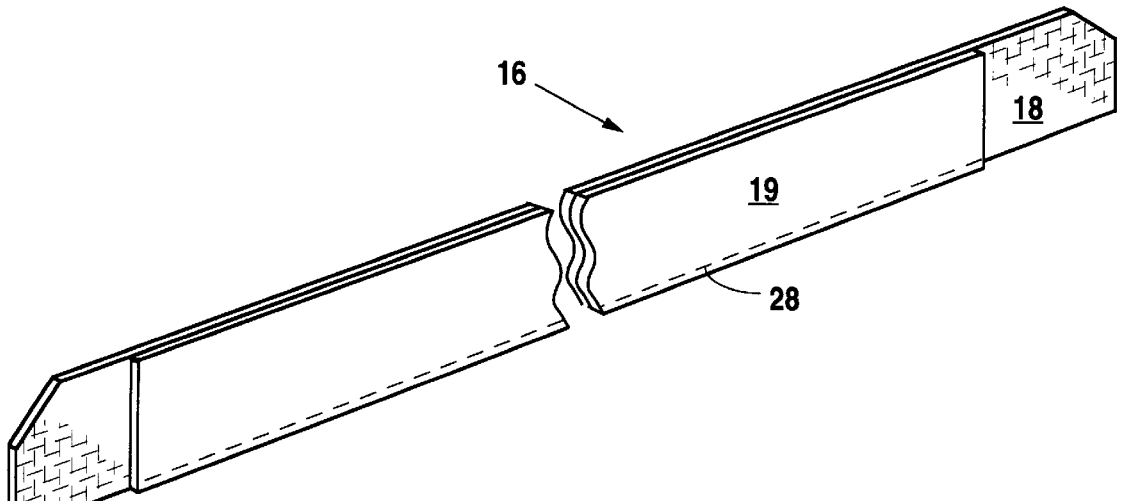
Fig. 5

REVERSIBLE VISOR AND ASSEMBLY METHOD THEREFOR

CROSS REFERENCE TO RELATED APPLICATIONS

This application is a divisional application of application Ser. No. 08/410,880 which was filed on Mar. 27, 1995 now U.S. Pat. No. 5,581,808.

BACKGROUND OF THE INVENTION

1. Field of the Invention

The present invention relates to visors and, more particularly, but not by of way of limitation, to a convertible visor and assembly method therefor.

2. Description of the Related Art

Visors typically consist of a bill attached to a headband that is placeable about the head of a wearer. Many hat wearers prefer visors because they lack a covering over the top of the head and, therefore, are lighter, cooler, and more comfortable than other hats.

Early visors included a bill attached to a hatband that completely encircled the wearer's head. An alternate design that eliminates the hatband employs a partial headband attached to a bill. Some visors utilizing partial headbands are manufactured from plastic in a single piece The side members of the partial headband comprise a plastic material sufficiently rigid to allow the engaging of the front, sides, and portions of the back part of the wearer's head. Unfortunately, some wearers find plastic visors undesirable because the plastic is uncomfortable when worn next to the skin.

U.S. Pat. No. 4,686,713 which issued Aug. 18, 1987 to Coleman, et al. improves over plastic visors by providing a cloth visor. The cloth includes a plastic partial headband enclosed within a cloth headband with the cloth and plastic headband being attached to a cloth bill enclosing plastic bill. The plastic partial headband and plastic bill provide the rigidity necessary to maintain the visor in place on a wearer's head, while the cloth enclosing the plastic headband and bill provide a soft and comfortable surface for contact with a wearer's skin. Although the visor disclosed in U.S. Pat. No. 4,686,713 provides a durable, high-quality cloth visor that is light, cool to the wearer and, very comfortable, a convertible visor that may be reversed to expose either surface of the visor to the exterior would provide a wearer with a more versatile two-in-one visor.

SUMMARY OF THE INVENTION

In accordance with the present invention, a convertible visor has a bill including a first bill covering attached to a second bill covering with a bill stiffener therebetween. A headband attaches to the bill and includes a first headband covering attached to a second headband covering with an overlap band attached to the first and second headband coverings. The first and second headband coverings define an enclosure therebetween that contains a headband stiffener. The first and second headband coverings each include a headband sheet attached to a wadding.

The bill stiffener permits the reversing of the bill to display either the first bill covering or the second bill covering as the exterior of the visor. Similarly, the first and second headband coverings define the enclosure to provide sufficient space between the first and second headband coverings and the headband stiffener to permit rotation of the first and second headband coverings about the headband stiffener. The first and second headband coverings rotate about the headband stiffener to permit the display of either the first headband covering or the second headband covering as the exterior of the visor.

In a method of manufacturing the convertible visor, a first bill covering is attached to a second bill covering with a bill stiffener therebetween to form a bill. A first headband covering is attached to the bill at the first bill covering, while a second headband covering is attached to the bill at the second bill covering. The first headband covering is attached to the second headband covering to form a passageway therebetween. An overlap band is attached to the first and second headband coverings. The first and second headband coverings are sealed at a first end to close a first end of the passageway. A headband stiffener is inserted into the passageway at a second end of the passageway. The first and second headband coverings are sealed at a second end to close the second end of the passageway.

It is therefore an object of the present invention to provide a convertible visor that is fully reversible to furnish wearers with extreme versatility by allowing them to obtain two different outer appearances from a single visor.

Still other objects, features, and advantages of the present invention will become evident to those of ordinary skill in the art in light of the following.

BRIEF DESCRIPTION OF THE DRAWINGS

FIG. 2 is a perspective view illustrating the assembly of the visor bill.

FIG. 3 is a cross-section view taken along lines 3,3 of FIG. 2 illustrating the assembly of the visor bill.

FIG. 4 is a cross-section illustrating the visor bill.

FIG. 5 is a perspective view illustrating a headband covering of the visor.

DETAILED DESCRIPTION OF THE PREFERRED EMBODIMENT

Figure 1:
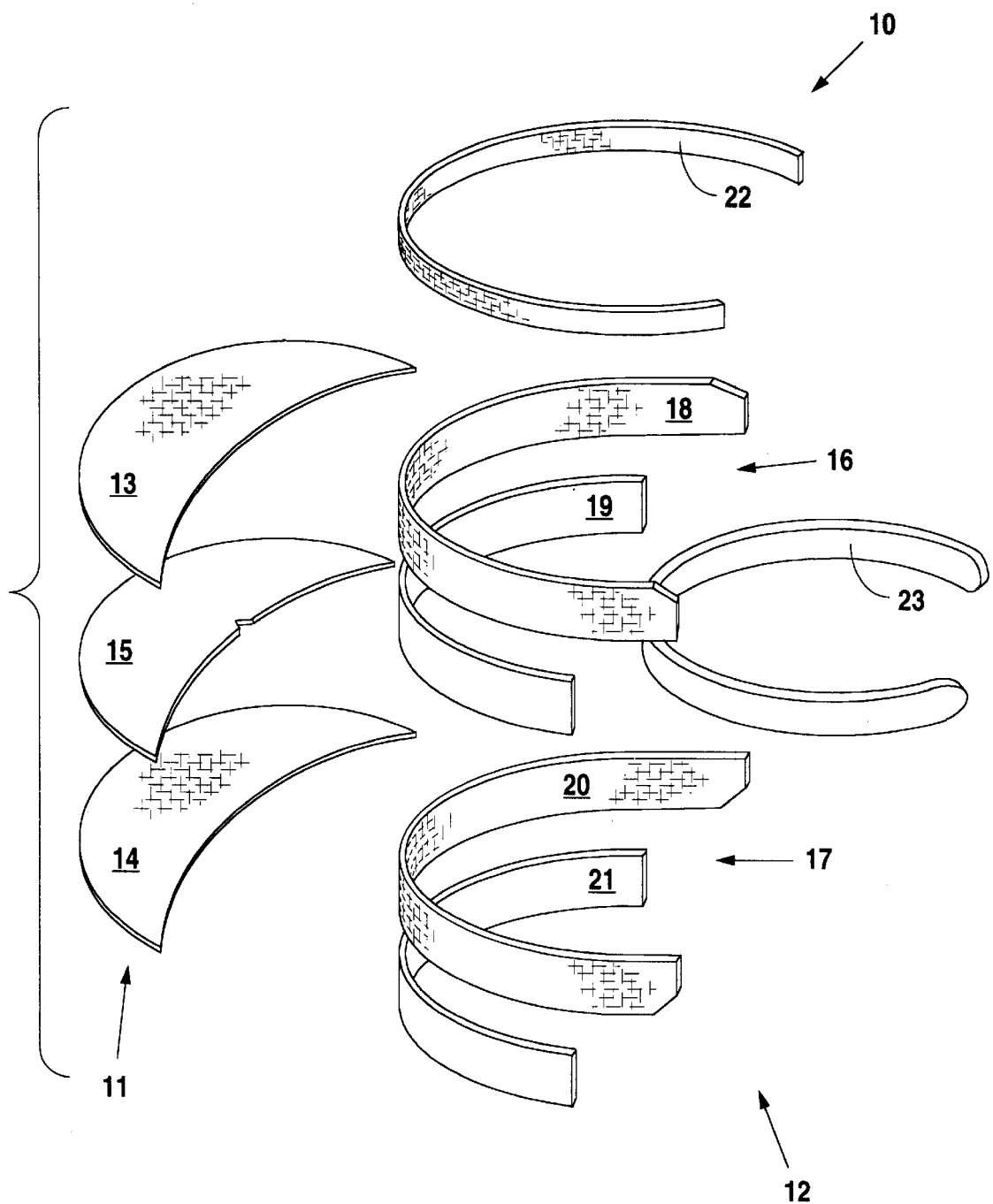
FIG. 1 is a perspective view illustrating each piece utilized in forming a convertible visor of the preferred embodiment.
Figure 11:
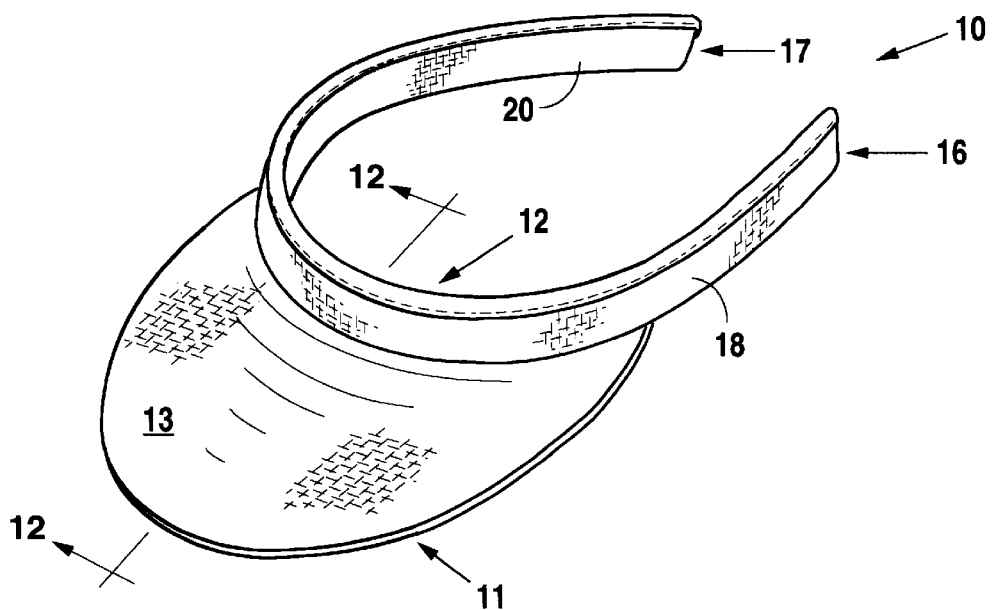
FIG. 11 is a perspective view illustrating a completed visor.
Figure 12:
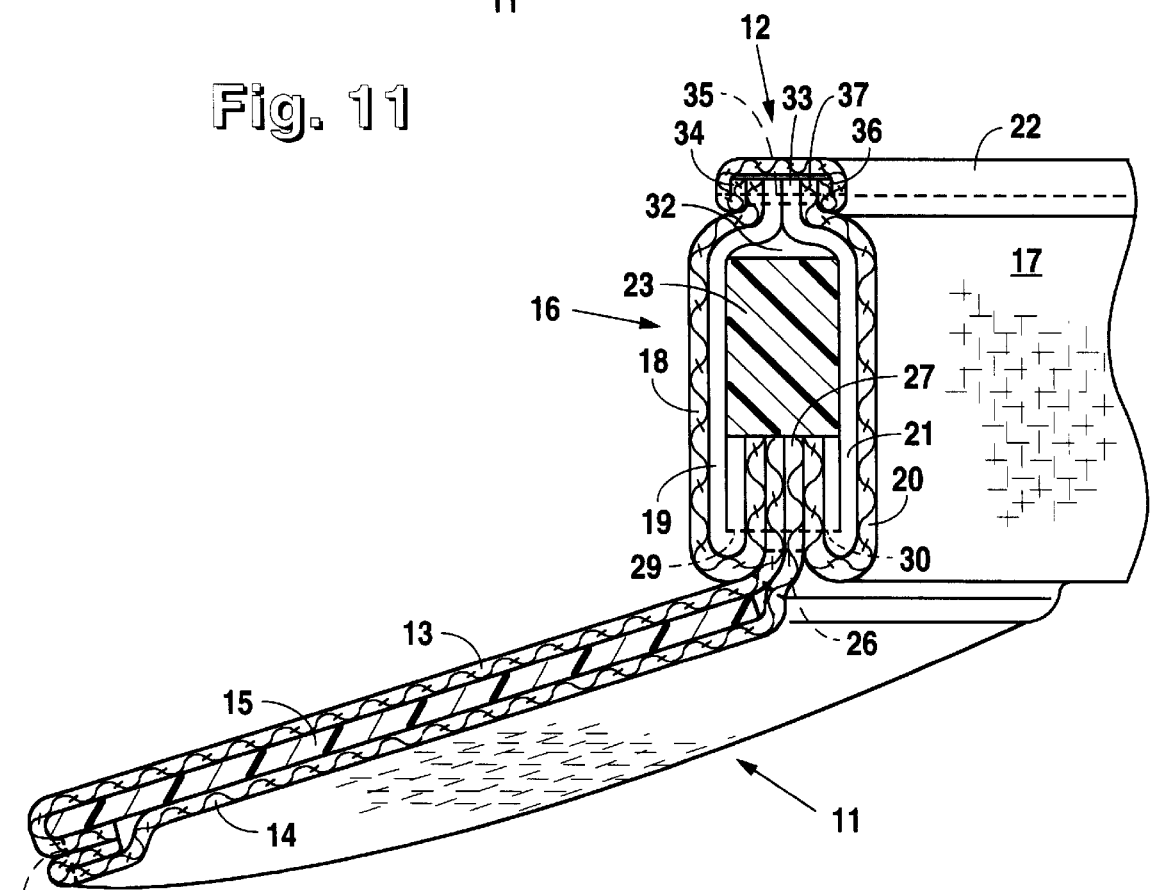
FIG. 12 is a cross-section view taken along lines 12,12 of FIG. 11 illustrating the completed visor.

Referring to FIGS. 1, 11, and 12, visor 10 includes bill 11 and headband 12. Bill 11 includes bill coverings 13 and 14 and bill stiffener 15. Bill coverings 13 and 14 may be any suitable fabric such as cloth or leather, while bill stiffener may be any flexible material such as a soft plastic.

Headband 12 includes headband coverings 16 and 17, overlap band 22, and headband stiffener 23. Headband covering 16 includes headband sheet 18 and wadding 19, while headband covering 17 includes headband sheet 20 and wadding 21. Headband sheets 18 and 20 and overlap band 22 may be any suitable fabric such as cloth or leather, while waddings 19 and 21 may be any suitable soft fabric such as cotton. Headband stiffener 23 may be any semi-rigid material such as hard plastic.

In this preferred embodiment bill covering 13 and headband sheet 18 have matching colors or colors that correspond to provide an aesthetically pleasing appearance. Similarly, bill covering 14 and headband sheet 20 have matching colors or colors that correspond to provide an aesthetically pleasing appearance. Overlap band 22 has a color that matches either bill covering 13 and headband covering 18 or bill covering 14 and headband covering 20. Alternatively, overlap band 22 has a color that corresponds with bill coverings 13 and 14 and headband coverings 18 and 20 to provide an aesthetically pleasing appearance. The colors of visor 10 are matched or correspond as described above because visor 10 is convertible in that it may be reversed to display either bill covering 13 and headband cove ring 18 as its exterior or bill covering 14 and headband covering 20 as its exterior. Regardless of which one of the bill coverings and headband coverings are displayed as the exterior of visor 10, overlap band 22 is always displayed as an exterior portion of visor 10.

Referring to FIG. 2, bill coverings 13 and 14 are aligned and then stitched together along seam 24. Referring to FIG. 3, once bill coverings 13 and 14 have been stitched together, they are turned inside out to place seam 24 to the interior thereby hiding it from view. Furthermore, bill coverings 13 and 14 define pocket 25 after their inversion. Referring to FIG. 4, pocket 25 receives bill stiffener 15 to provide bill 11 with a support member for bill coverings 13 and 14. However, bill stiffener 15 provides sufficient flexibility to permit the reversing of bill 11 to place either bill covering 13 or bill covering 14 to the exterior of visor 10. To complete the formation of bill 11, bill coverings 13 and 14 are stitched a seam 26 to seal pocket 25 and create flap 27.

Referring to FIG. 5, headband covering 16 is formed by stitching wadding 19 to headband sheet 18 along seam 28. Headband covering 16 includes wadding 19 to provide a cushion between headband stiffener 23 and the wearer. The fashioning of headband covering 17 has not been described because it is identical to that of headband covering 16.

Figure 6:
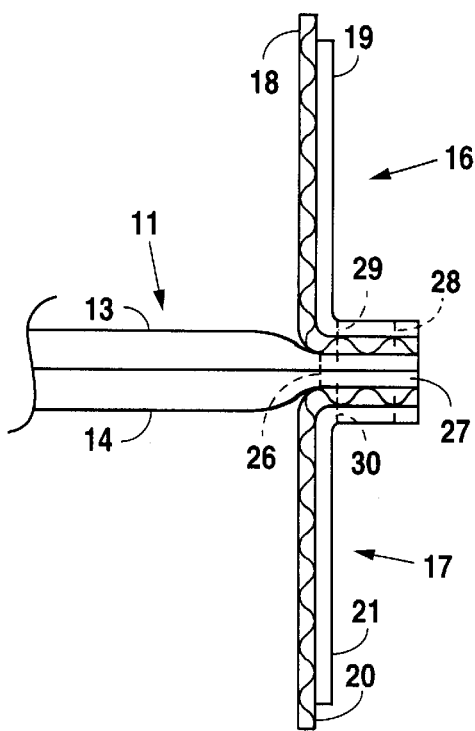
FIG. 6 is a side view in partial cross-section illustrating the attachment of the headband coverings to the bill.

Referring to FIG. 6, a first edge of headband covering 16 is aligned with flap 27 at bill covering 13 and then stitched thereto along seam 29. Similarly, a first edge of headband covering 17 is aligned with flap 27 at bill covering 14 and then stitched thereto along seam 30. Headband coverings 16 and 17 are stitched on opposite sides of flap 27 to accomplish the securing the headband 12 to bill 11 and to hide flap 27 in the interior of visor 10. After the stitching of headband coverings 16 and 17 to bill 11, the portions of the first edges of headband coverings 16 and 17 that extend beyond bill 11 are aligned and then stitched together.

Figure 7:
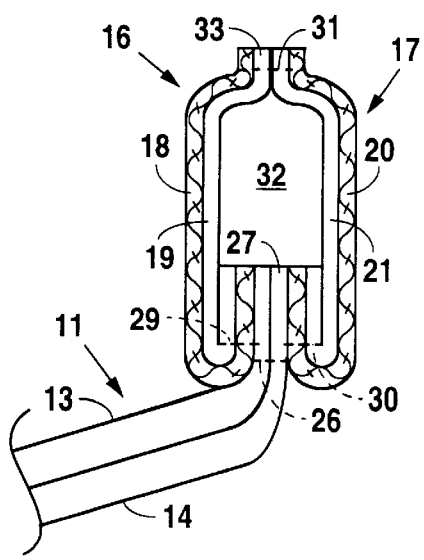
FIG. 7 is a side view in partial cross-section illustrating the attachment together of the headband coverings.

Referring to FIG. 7, the second edges of headband coverings 16 and 17 are folded together and aligned so that they may be stitched together along seam 31 to form passageway 32. Passageway 32 is formed because, although headband covering 16 and 17 are stitched together along their first and second edges, the ends of headband coverings 16 and 17 remain unstitched. Additionally, the stitching together of the second edges of headband coverings 16 and 17 results in the formation of flap 33.

Figure 8:
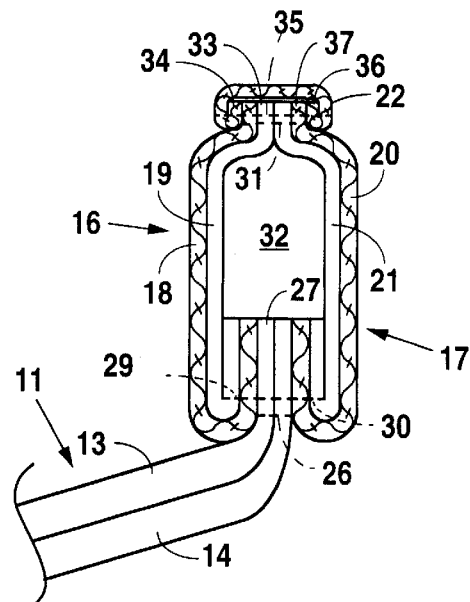
FIG. 8 is a side view in partial cross-section illustrating the attachment of the overlap band to the headband coverings.

Referring to FIG. 8, overlap band 22 is utilized to cover flap 33. To attach overlap band 22 to headband coverings 16 and 17, edge 34 of overlap band 22 is first folded to the interior of overlap band 22 and then position against flap 33. Second, the side of overlap band 22 including edge 34 is stitched to flap 33 a long seam 35. Third, edge 36 of overlap band 22 is folded to the interior of overlap band 22 and then position against flap 33. Finally, the side of overlap band 22 including edge 36 is stitched to flap 33 along seam 37. Edges 34 and 36 of overlap band 22 are folded toward the interior to provide the appearance of a hidden seam. After the stitching of overlap band 22 to headband coverings 16 and 17,the portions of overlap band 22 that extend beyond headband coverings 16 and 17 are stitched together.

Figure 10:
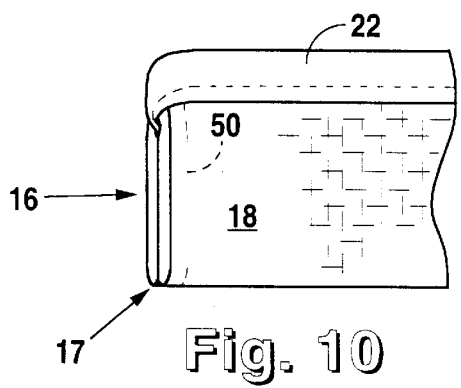
FIG. 10 is side view illustrating the sealing of the headband coverings and overlap band at the rear of the visor.

Referring to FIG. 10, a first end of passageway 32 must be closed before the insertion of headband stiffener 23. To close the first end of passageway 32, first ends of headband coverings 16 and 17 are folded to the interior so that the appearance of a hidden seam is produced. Furthermore, a first end of overlap band 22 that extends beyond the first ends of headband coverings 16 and 17 is inserted into passageway 32 along with the first ends of headband coverings 16 and 17. The first ends of headband coverings 16 and 17 including the first end of overlap band 22 are then stitched together along seam 50 to seal the first end of passageway 32 and produce the appearance of a hidden seam.

Figure 9:
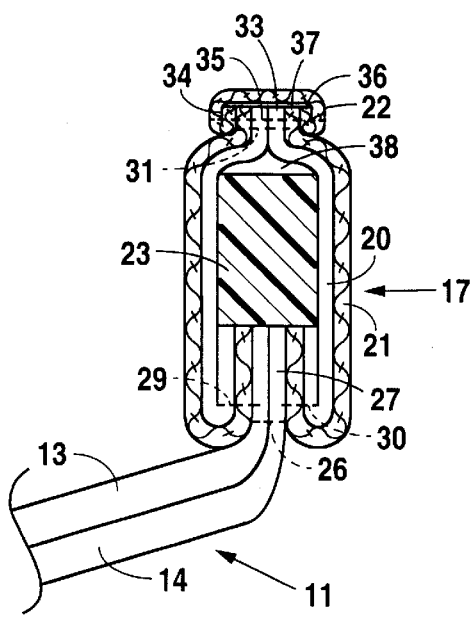
FIG. 9 is a side view in partial cross-section illustrating the insertion of the headband stiffener between the headband coverings.

Referring to FIG. 9, after the sealing of the first end of passageway 32, headband stiffener 23 is inserted into passageway 32 through the second end of passageway 32 until it resides completely therein. Once headband stiffener 23 has been inserted into passageway 322, the second ends of headband coverings 16 and 17 including the second end of overlap band 22 are folded into passageway 32. The second ends of headband coverings 16 and 17 including the second end of overlap band 22 are then stitched together to seal the second end of passageway 32 and produce the appearance of a hidden seam. The sealing of passageway 32 creates enclosure 38 between headband coverings 16 and 17. Enclosure 38 contains headband stiffener 23 within headband 12, however, headband coverings 16 and 17 define enclosure 38 with sufficient space between headband coverings 16 and 17 and headband stiffener 23 to permit a rotation of headband coverings about headband stiffener 23 that allows the display of either headband covering 16 or headband covering 17 as the exterior of visor 10.

Referring to FIGS. 11 and 12, the reversing of visor 10 to place bill covering 14 and headband covering 17 to the exterior first requires a wearer flip bill 11 inside out to place bill covering 14 as the exterior of visor 10 and bill covering 13 as the interior. That turning of bill 11 inside out places the outer edge of bill 11 above headband 12 with headband covering 16 still facing to the exterior of visor 12. However, due to the increased size of enclosure 38 that does not firmly press headband stiffener 23 against headband coverings 16 and 17, headband coverings 16 and 17 may be rotated around headband stiffener 23 such that brim stiffener 23 rotates above bill 11. As the wearer continues to rotate headband coverings 16 and 17 about brim stiffener 23, headband covering 17 passes around brim stiffener 23 to form the exterior of visor 10, while headband covering 16 passes around brim stiffener 23 to form the interior of visor 10. Additionally, the rotation of headband coverings 16 and 17 about headband stiffener 23 brings overlap band 22 to a position above brim stiffener 23. Finally the ends of headband coverings 16 and 17 are rotated about brim stiffener 23 to complete the placement of headband 17 as the exterior of visor 10 and headband covering 16 as the interior of visor 10. The above steps may be repeated to again place bill covering 13 and headband covering 16 as the exterior of visor 10. Thus, visor 10 provides extreme versatility to a wearer because it permits the wearer to obtain two different outer appearances from a single visor.

Figure 13:
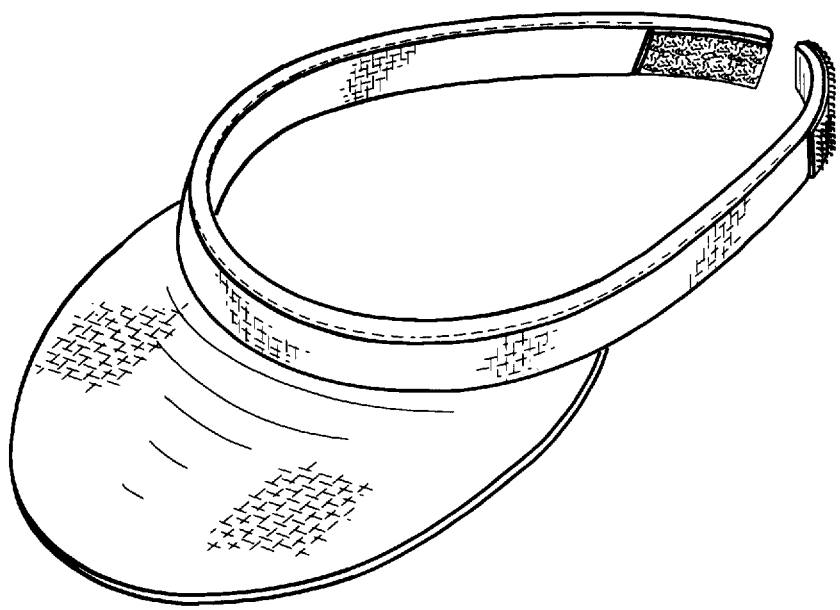
FIG. 13 is a perspective view illustrating an alternative embodiment of the visor.

In an alternative embodiment illustrated in FIG. 13, visor 10 may be provided with a headband that completely encircles the head of a wearer to provide a visor for the more active person. The construction of the alternative visor is the same as described above, except the headband sheets, their respective waddings, and the overlap band extend beyond the headband stiffener such that they will overlap at the rear of a wearer's head. After the formation of the passageway and the sealing of one of its ends as previously described, the headband stiffener is inserted and positioned at the front of the headband. The opposite end of the passageway is then closed as previously described to create the enclosure for the headband stiffener. However, in this alternative embodiment, an attachment device such as VELCRO™ or a snap is placed on each portion of the headband coverings that extend beyond the headband stiffener to permit their fastening together at the rear of the wearer's head. With the headband completely encircling and fastenend at the rear of a wearer's head, the visor will remain in place even during more dynamic activities such as tennis.

Although the present invention has been described in terms of foregoing embodiment, such description is been for exemplary purposes only and, as will be apparent to those of ordinary skills in the art, many alternatives, equivalents, and variations of varying degrees will fall within the scope of the present invention. That scope, accordingly, is not to be limited in any respect by the foregoing description, rather, it is defined only by the claims that follow.

I claim:

1. A method of manufacturing a convertible visor, comprising the steps of:

attaching a first bill covering to a second bill covering with a bill stiffener therebetween to form a bill wherein said bill is reversible to display either said first bill covering or said second bill covering as the exterior of said visor;

attaching a first headband covering to said bill at said first bill covering;

attaching a second headband covering to said bill at said second bill covering;

attaching said first headband covering to said second headband covering to form a passageway therebetween;

sealing said first and second headband covering at a first end to close a first end of said passageway;

inserting a headband stiffener into said passageway at a second end of said passageway;

sealing said first and second headband coverings at a second end to close said second end of said passageway and form an enclosure that contains said headband stiffener wherein said enclosure includes space sufficient to allow the rotation of said first and second headband coverings about said headband stiffener to permit the display of either said first headband covering or said second headband covering as the exterior of said visor.

2. The method according to claim 1 further comprising the step of attaching an overlap band to said first and second headband coverings.

3. The method according to claim 1 further comprising the step of attaching a headband sheet to a wadding to form each of said first and second headband coverings.

4. The method according to claim 1 further comprising the step of securing a fastening means to said first and second headband coverings to permit their connection at the rear of a wearer's head.

* * * * *